United States Patent
Starkenmann et al.

(10) Patent No.: US 9,550,960 B2
(45) Date of Patent: Jan. 24, 2017

(54) COMPOUNDS FOR A CONTROLLED RELEASE OF ACTIVE MOLECULES

(71) Applicant: FIRMENICH SA, Geneva (CH)

(72) Inventors: Christian Starkenmann, Geneva (CH); Myriam Troccaz, Saint-Julien-en-Genevois (FR); Fabienne Mayenzet, Geneva (CH)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 14/899,556

(22) PCT Filed: Jun. 6, 2014

(86) PCT No.: PCT/EP2014/061909
§ 371 (c)(1),
(2) Date: Dec. 17, 2015

(87) PCT Pub. No.: WO2014/202416
PCT Pub. Date: Dec. 24, 2014

(65) Prior Publication Data
US 2016/0137952 A1     May 19, 2016

(30) Foreign Application Priority Data

Jun. 17, 2013    (EP) .................................. 13172277

(51) Int. Cl.
| | | |
|---|---|---|
| *A61K 8/60* | (2006.01) | |
| *C11B 9/00* | (2006.01) | |
| *A61Q 13/00* | (2006.01) | |
| *C11D 3/50* | (2006.01) | |
| *A61Q 15/00* | (2006.01) | |
| *C11D 3/386* | (2006.01) | |

(52) U.S. Cl.
CPC .............. *C11B 9/008* (2013.01); *A61K 8/602* (2013.01); *A61Q 13/00* (2013.01); *A61Q 15/00* (2013.01); *C11B 9/0003* (2013.01); *C11B 9/0076* (2013.01); *C11D 3/38636* (2013.01); *C11D 3/507* (2013.01); *A61K 2800/56* (2013.01)

(58) Field of Classification Search
None
See application file for complete search history.

(56) References Cited

U.S. PATENT DOCUMENTS

| | | |
|---|---|---|
| 4,822,603 A | 4/1989 | Farris et al. |
| 2010/0129795 A1 | 5/2010 | Pris et al. |
| 2010/0132073 A1* | 5/2010 | Caputi .................... A23L 1/034 800/298 |

FOREIGN PATENT DOCUMENTS

| | | |
|---|---|---|
| EP | 24175 B1 | 7/1983 |
| EP | 384034 A2 | 8/1990 |
| EP | 468564 A2 | 1/1992 |
| WO | WO9900377 A1 | 1/1999 |
| WO | WO0189464 A1 | 11/2001 |
| WO | WO2006079934 A2 | 8/2006 |

OTHER PUBLICATIONS

Schulz et al., "Headspace solid-phase microextraction-gas chromatography-mass spectrometry for the quantitative determination of the characteristic flavouring agent eugenol in serum samples after enzymatic cleavage to validate post-offence alcohol drinking claims", J Chromatography A 1211: 113-119 (2008).*
Merck Index—farnesol.*
Murphy, "Direct synthesis of a glucosiduronic acid. Specific complexing of copper among biological cations", J Pharmaceut Sci 61:810-811 (1972).*
Nolan et al., "Menthol-beta-D-glucuronide: a potential prodrug for treatment of the irritable bowel syndrome", Pharm Res 11: 1707-1711 (1994).*
International Preliminary Report on Patentability, Appl. No. PCT/EP2014/061909, Dec. 22, 2015.
International Search Report and Written Opinion, application PCT/EP2014/061909, mailed Oct. 2, 2014.
Brenner et al., J. Bacteriol. 1972, 109, 3, 953-965.
Hawksworth et al., J. Med. Microbiol. 1971, 4, 451-45.
Natsch et al., Flavour Fragr. J. 2013, 28, 262-268.
Sammons et al._Studies in detoxication_The metabolism of vanillin and vanillic acid in the rabbit_Bio J.—vol. 35, No. 10-11, p. 1175-89.

* cited by examiner

*Primary Examiner* — Sue Liu
*Assistant Examiner* — Thor Nielsen
(74) *Attorney, Agent, or Firm* — Winston & Strawn LLP

(57) ABSTRACT

The present invention relates to the field of perfumery. More particularly, it concerns compounds comprising at least one β-glucuronide moiety capable of liberating a perfuming alcohol. The present invention concerns also the use of said compounds in perfumery as well as the perfuming compositions or perfumed articles, in particular deodorants or antiperspirants comprising the invention's compounds.

17 Claims, No Drawings

COMPOUNDS FOR A CONTROLLED RELEASE OF ACTIVE MOLECULES

TECHNICAL FIELD

The present invention relates to the field of perfumery. More particularly, it concerns compounds comprising at least one β-glucuronide moiety capable of liberating odorant molecules in particular alcohols through the action of skin microflora or of a bacteria from the environment. The present invention also concerns the use of said compounds in perfumery as well as perfuming compositions or perfumed articles in particular deodorants and antiperspirants comprising the invention's compounds.

PRIOR ART

Compounds which are capable of liberating an active ingredient such as an odoriferous compound under certain conditions, thus allowing differing and/or prolonging the effect of the active ingredient over a certain period of time, have been of high interest for the perfumery industry. These compounds often referred to as "pro-perfumes" when the active ingredient is odorant, can be used in various applications, for example in fine or functional perfumery. Pro-perfumes have been for instance described as very useful in the washing of textiles, a particular field in which there is a constant quest to enable the effect of perfumes to be effective for a certain period of time after washing and drying.

The release of active molecules from pro-perfumes happens during a so-called decomposition reaction. Said reaction which leads to the release of e.g. odoriferous molecules, have been described as being possibly influenced by pH changes, the presence of oxygen or other oxidants, enzymes or heat, but may be triggered by other types of mechanisms or the combination of several mechanisms.

More recently, the use of pro-perfumes in deodorants, exploiting a release generated by skin bacteria through an enzymatic pathway, has been the object of public disclosures. Based on known precursors of malodorous volatile acids, glutamine conjugates and their ability to release a fragrance molecule instead of a malodor compound upon decomposition by a specific malodor-forming enzyme, namely corynebacterial $N^\alpha$-acyl-glutamine-aminoacylase targeting applications in deodorant have been described in vitro and tested in vivo by Natsch et al in Validation of a malodour-forming enzyme as a target for deodorant active: in vivo testing of a glutamine conjugate targeting a cornebacterial Na-acyl-glutamine-aminoacylase, Flavour and Fragrance Journal, 2013.

Malodor control is a key issue for the perfumery industry. While some precursors of body odors in particular human sweat have been well described in the past, such as glutamine conjugates and cysteine-S-conjugates described by Natsch et al., and cysteine-glycine-S-conjugates described by Starkenmann et al. in WO 2006/079934, others, in particular steroids have not been unambiguously identified in the literature.

Amongst the compounds of the present invention, only a few are known from the prior art. Said known compounds are phenethyl β-D-glucopyranosiduronic acid; β-D-glucopyranosiduronic acid 4-(3-oxobutyl)phenyl; glucopyranosiduronic acid 1-menthyl; β-D-glucopyranosiduronic acid 4-formyl-2-methoxyphenyl; and β-D-glucopyranosiduronic acid 2-methoxy-4-(2-propen-1-yl)phenyl. These compounds have either been either found in nature or used in a different context than perfumery. In particular, in the documents citing those compounds, there is no mention or suggestion of their potential use as perfuming ingredients and more specifically of the use of said compounds to control the release of active, e.g. odoriferous molecules.

There is still a high interest from the perfuming industry for finding new and more effective pro-perfumes. On the other hand, malodor control is a key issue for the industry and effective solutions to combat malodors such as those coming from body sweat are therefore needed.

DESCRIPTION OF THE INVENTION

Compounds comprising at least a β-glucuronide moiety, which are capable of liberating an active molecule upon the action of certain bacteria, in particular skin bacteria found in human sweat but also bacteria found in the environment, have now surprisingly been discovered. As "active molecule" it is meant here any molecule capable of bringing an odor benefit or effect into its surrounding environment, and in particular an odoriferous molecule, i.e. a perfuming ingredient, such as an alcohol. In the context of the invention, a "perfuming ingredient" is a compound, which is of current use in the perfumery industry, i.e. a compound which is used as active ingredient in perfuming preparations or compositions in order to impart a hedonic effect. In other words, such a perfuming ingredient must be recognized by a person skilled in the art of perfumery as being able to impart or modify in a positive or pleasant way the odor of a composition, and not just as having an odor. The invention's compounds are thus valuable perfuming ingredients, particularly useful in applications such as deodorants and antiperspirants, wherein they are going to be in contact with a bacteria susceptible to cleave them and release the active perfuming alcohol.

Therefore a first aspect of the present invention concerns the use as a perfuming ingredient of a compound of formula

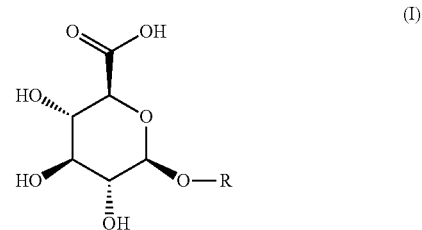

wherein:
R represents a perfuming alcohol preferably selected from the group consisting of 4-allyl-2-methoxyphenol (eugenol), 3-benzyl-3-pentanol, 4-cyclohexyl-2-methylbutan-2-ol (origin: Firmenich SA, Geneva, Switzerland), 2-cyclohexylpropanol, decanol, 9-decenol (Rosalva, origin: International Flavors and Fragrances, New York, USA), (2,4-dimethylcyclohex-3-enyl)methanol, (2,4-dimethylcyclohexyl)methanol, 2-(1,1-dimethylethyl)-4-methylcyclohexanol, 2,6-dimethylheptan-2-ol, 3,7-dimethyl-7-hydroxyoctanal, 2,5-dimethyl-2-indanmethanol, 3,7-dimethyl-1,6-nonadien-3-ol, 6,8-dimethylnonan-2-ol, 4,8-dimethyl-7-nonen-2-ol, (E)-3,7-dimethyl-2,6-octadienol (geraniol), (Z)-3,7-dimethyl-2,6-octadienol (nerol), 3,7-dimethyl-3,6-octadienol, 3,7-dimethyl-1,6-octadien-3-ol (linalool), 3,7-dimethyloctane-1,7-diol (hydroxycitronellol), 3,7-dimethyloctanol, 2,6-dimethyloctan-2-ol (tetrahydromyrcenol), 3,7-dimethyloctan-3-ol, 3,7-dimethylocten-3-ol, 3,7- dimethyloct-6-enol (citronellol), 3,7-dimethyloct-7-enol, 2,6-dimethyloct-7-en-2-ol (dihydromyrcenol), (E)-3,3-dimethyl-5-(2,2,3-trimethyl-3-cyclopenten-1-yl)-4-penten-2-ol (Polysantol®, origin: Firmenich SA, Geneva, Switzerland), dodecanol, 1,8-epoxy-p-menthane (eucalyptol), 2-ethoxy-5-(1-propenyl)phenol, 2-ethyl-1-hexanol, ethyl 3-hydroxy hexanoate, 4-ethyl-2-methoxyphenol, 6-ethyl-3-methyl-5-octenol, 5-ethylnonan-2-ol, 2-ethyl-4-(2,2,3-trimethylcyclopent-3-enyl)but-2-enol, 1-heptanol, hexanol, hexan-2-ol, 3-hexenol, 4-hexenol, 3-hydroxybutan-2-one, 4-hydroxy-3-ethoxybenzaldehyde (ethylvanillin), 4-hydroxy-3-methoxybenzaldehyde (vanillin), 4-(4-hydroxy-3-methoxyphenyl)butan-2-one, 2-(hydroxymethyl)nonan-2-one, 4-(4-hydroxy-1-phenyl)butan-2-one (raspberry ketone), 1-(N-indolyl)-3,7-dimethyloctane-1,7-diol, 4-isopropyl-1-benzenemethanol, 4-isopropylcyclohexanol, 1-(4-isopropyl-1-cyclohexyl)ethanol, (4-isopropyl-1-cyclohexyl)methanol, 2-isopropyl-5-methylphenol, 5-isopropyl-2-methylphenol, (4-isopropylphenyl)methanol, 7-p-menthanol (Mayol®, origin: Firmenich SA, Geneva, Switzerland), p-menthan-3-ol (menthol), p-menthan-8-ol, p-menthen-4-ol, p-menthen-8-ol, p-menth-8-enol, p-menth-8-en-2-ol, p-menth-8-en-3-ol, 4-methoxy-1-benzenmethanol, 7-methoxy-3,7-dimethyloctan-2-ol, 2-methoxy-4-methylphenol, 2-methoxyphenol, 2-methoxy-2-phenylethanol, (4-methoxyphenyl)methanol (anisyl alcohol), 2-methoxy-4-(1-propenyl)phenol (isoeugenol), 2-methoxy-4-propyl-1-cyclohexanol (Tarragol®, origin: Firmenich SA, Geneva, Switzerland), 2-methoxy-4-propylphenol, 2-methoxy-4-vinylphenol, 3-(4-methylcyclohex-3-enyl)butanol, 4-methyl-3-decenol, 4-methyl-3-decen-5-ol (origin: Givaudan SA, Geneva, Switzerland), 4-(1-methylethyl)cyclohexylmethanol, 4-methylphenol, 2-methyl-4-phenylbutan-2-ol, 3-methyl-4-phenylbutan-2-ol, 1-(4-methylphenyl)ethanol, 2-(2-methylphenyl)ethanol, 2-methyl-4-phenylpentanol, 2-methyl-5-phenylpentanol, 3-methyl-5-phenylpentanol (phenylhexanol, origin: Firmenich SA, Geneva, Switzerland), 4-methyl-1-phenylpentan-2-ol, 2-methyl-1-phenylpropan-2-ol, 2-(4-methylphenyl)propan-2-ol, 3-methyl-5-(2,2,3-trimethyl-3-cyclopenten-1-yl)-4-penten-2-ol (Ebanol®, origin: Givaudan SA, Geneva, Switzerland), 2-(2-methylpropyl)-4-hydroxy-4-methyl-tetrahydropyrane, 2-methyl-4-(2,3,3-trimethyl-2-cyclopenten-1-yl)-2-butenol (Santalife, origin: International Flavors and Fragrances, New York, USA), 3-methyl-5-(2,2,3-trimethyl-3-cyclopenten-1-yl)pentan-2-ol, 2-methyl-4-(2,2,3-trimethyl-3-cyclopenten-1-yl)pent-4-enol, 3-methyl-5-(2,2,3-trimethylcyclopentyl-3-enyl)pent-4-en-2-ol, 2,6-nonadienol, 1-nonanol, 6-nonenol, 1,2,3,4,4a,5,8,8a-octahydro-2,2,6,8-tetramethyl-1-naphthalenol, octahydro-2,5,5-trimethyl-2-naphthalenol, octanol, octan-2-ol, octan-3-ol, 1-octen-3-ol, 3,4,5,6,6-pentamethylheptan-2-ol (Kohinool®, origin: International Flavors and Fragrances, New York, USA), 2-pentyl-1-cyclopentanol, perhydro-4,8a-dimethyl-4a-naphthalenol, 2-phenoxyethanol, 4-phenylbutan-2-ol, 4-phenyl-3-buten-2-ol, 1-phenylethanol, 2-phenylethanol, 1-phenylhexan-2-ol, phenylmethanol, 1-phenylpentan-2-ol, 2-phenylpropanol, 2-phenylpropanol, 3-phenylpropanol, 1-phenylpropan-2-ol, 3-phenyl-2-propenol, 2-tert-butylcyclohexanol (Verdol, origin International Flavors and Fragrances, New York, USA), 4-tert-butylcyclohexanol, 1-(2-tert-butyl-cyclohexyloxy)butan-2-ol, 2-tert-butyl-4-methyl-1-cyclohexanol, tetrahydro-2-isobutyl-4-methyl(2H)pyran-4-ol (Florol®, origin: Firmenich SA, Geneva, Switzerland), 2-(tetrahydro-5-methyl-5-vinyl-2-furyl)propan-2-ol, 1-(2,2,3,6-tetramethylcyclohex-1-yl)hexan-3-ol (Limbanol®, origin: Firmenich SA, Geneva, Switzerland), 2,4,6,8-tetramethyl-nonan-1-ol, 3,6,7-tetramethylnonan-1-ol, 2,6,10,10-tetramethyl-1-oxaspiro[4.5]decan-6-ol, 2,6,6,8-tetramethyltricyclo[5.3.1.0(1,5)]undecan-8-ol (cedrenol), (+)-(1R,2R)-1,3,3-trimethylbicyclo[2.2.1]heptan-2endo-ol (fenchol), (+)-(1R, 2S)-1,7,7-trimethylbicyclo[2.2.1]heptan-2-ol (borneol), 2,6,6-trimethylbicyclo[3.1.1]heptan-3-ol, 3-(5,5,6-trimethylbicyclo[2.2.1]hept-2-yl)cyclohexanol (Sandela®, origin: Givaudan SA, Geneva, Switzerland), 4-(5,5,6-trimethylbicyclo[2.2.1]hept-2-yl)cyclohexanol, 3,3,5-trimethyl-cyclohexanol, 4-(2,6,6-trimethyl-2-cyclohexen-1-yl)butan-2-ol, 4-(2,6,6-trimethyl-1-cyclohexen-1-yl)-3-buten-2-ol (beta-ionol), (E)-4-(2,6,6-trimethyl-2-cyclohexen-1-yl)-3-buten-2-ol (alpha-ionol), (2,4,6-trimethylcyclohex-3-enyl)methanol, 1-(2,2,6-trimethyl-1-cyclohexyl)hexan-3-ol, 5-(2,2,3-trimethyl-3-cyclopentenyl)-3-methylpentan-2-ol, 4,7,9-trimethyldecan-2-ol, 4,6,8-trimethyldecan-2-ol, 3,8,9-trimethyldecan-2-ol, 3,7,11-trimethyl-2,6,10-dodecatrienol (farnesol), 3,7,11-trimethyl-1,6,10-dodecatrien-3-ol (nerolidol), 3,3,5-trimethylhexanol, undecanol and undecan-2-ol and 10-undecenol.

Compounds of formula (I) are referred to as β-glucuronides conjugates.

According to a preferred embodiment, R is selected from the group consisting of (E)-3,7-dimethyl-2,6-octadienol (geraniol), 3,7-dimethyl-1,6-octadien-3-ol (linalool), 3,7-dimethyloct-6-enol (citronellol), 2,6-dimethyloct-7-en-2-ol (dihydromyrcenol), 3-hexenol, 2-phenylethanol, (E)-3,3-dimethyl-5-(2,2,3-trimethyl-3-cyclopenten-1-yl)-4-penten-2-ol (Polysantol®, origin: Firmenich SA, Geneva, Switzerland), 7-p-menthanol (Mayol®, origin: Firmenich SA, Geneva, Switzerland), 3-methyl-5-phenylpentanol (phenylhexanol, origin: Firmenich SA, Geneva, Switzerland), 2,6-nonadienol, 1-phenylhexan-2-ol, tetrahydro-2-isobutyl-4-methyl(2H)pyran-4-ol (Florol®, origin: Firmenich SA, Geneva, Switzerland), 3-(5,5,6-trimethylbicyclo[2.2.1]hept-2-yl)cyclohexanol (Sandela®, origin: Givaudan SA, Geneva, Switzerland), 3-(4-methylcyclohex-3-enyl)butanol, 4-cyclohexyl-2-methylbutan-2-ol (coranol), 4-methyl-3-decen-5-ol (undecavertol), 4-allyl-2-methoxyphenol (eugenol), 4-(4-hydroxy-1-phenyl)butan-2-one (raspberry ketone), p-menthan-3-ol (menthol), 4-hydroxy-3-methoxybenzaldehyde (vanillin), 3,7-dimethyl-1,6-nonadien-3-ol (ethyl linalool), 3,7-dimethyloctanol, 1-(2,2,6-trimethyl-1-cyclohexyl)hexan-3-ol (Norlimbanol®, origin: Firmenich SA, Geneva, Switzerland), 2-ethyl-4-[2,2,3-trimethylcyclopent-3-enyl)but-2-enol (Dartanol®, origin: Firmenich SA, Geneva, Switzerland), (E)-3,3-dimethyl-5-(2,2,3-trimethyl-3-cyclopenten-1-yl)-4-penten-2-ol (Polysantol®, origin: Firmenich SA, Geneva, Switzerland) and 2-(1,1-dimethylethyl)-4-methylcyclohexanol.

Even more preferably, R is selected from the group consisting of 4-allyl-2-methoxyphenol (eugenol), 4-(4-hydroxy-1-phenyl)butan-2-one (raspberry ketone), p-menthan-3-ol (menthol), 4-hydroxy-3-methoxybenzaldehyde (vanillin), 2-phenylethanol, 3,7-dimethyloct-6-enol (citronellol) and 2,6-dimethyloct-7-en-2-ol (dihydromyrcenol).

The compounds of the invention turned out to be capable of producing odorant molecules in particular when in contact with specific bacteria. Advantageously, the compounds of the invention are cleaved under the action of the skin microflora. For example these compounds are susceptible of releasing a perfuming alcohol when incubated with bacteria that have been identified in human sweat, which makes them particularly useful for an application in deodorants or antiperspirants.

Bacteria susceptible of cleaving compounds of formula (I) are bacteria having the gene encoding for the β-glucuronidase enzyme (uidA). Non limiting example of suitable bacteria include those belonging to a family selected from Enterobacteriaceae and the genera *Corynebacterium, Propionibacterium, Streptococcus, Lactobacillus, Bifidobacterium, Clostridium, Bacteroides* and *Corynebacterium*. In particular, such bacteria have been identified as one selected from *Propionibacterium acnes, Streptococcus agalactiae, Escherichia coli, Escherichia fergusonii, Staphylococcus warneri, Staphylococcus xylosus, Staphyloccocus haemolyticus, Streptococcus agalactiae, Escherichia coli, Escherichia fergusonii, Corynebacterium glucuronolyticum* and *Bifidobacterium denticum* [Hawksworth, G., B. S Drasar, and M. J. Hill. 1971. Intestinal bacteria and the hydrolysis of glycosidic bounds. J. Med. Microbiol. 4:451-45] [Brenner, D. J., Fanning, G. R., Skerman, F. J., Falkow, S., 1972. Polynucleotide sequence divergence among strains of *Escherichia coli* and closely related organisms. J. Bacteriol. 109, 953-965].

However, other bacteria e.g. found in the environment are also capable of cleaving the compounds of the invention.

Compounds of formula (I) as defined above, constitute another object of the present invention provided that phenethyl β-D-glucopyranosiduronic acid; β-D-glucopyranosiduronic acid 4-(3-oxobutyl)phenyl; glucopyranosiduronic acid 1-menthyl; β-D-glucopyranosiduronic acid 4-formyl-2-methoxyphenyl; and β-D-glucopyranosiduronic acid 2-methoxy-4-(2-propen-1-yl)phenyl are excluded. These compounds may be synthesized from commercially available ingredients. Generally speaking, glucuroside conjugates of formula (I) are obtainable by oxidation of corresponding glucoside conjugates. Particular examples are described herein below. Another possibility is to react an acetylated glucuronide methyl ester via the imidate with the odorant alcohol.

As mentioned above, the invention concerns the use of a compound of formula (I) as a perfuming ingredient. In other words, it concerns a method to confer, enhance, improve or modify the odor properties of a perfuming composition or of a perfumed article, which method comprises adding to said composition or article an effective amount of at least one compound of formula (I). By "use of a compound of formula (I)" it has to be understood here also the use of any composition containing a compound (I) and which can be advantageously employed in perfumery industry.

Said compositions, which in fact can be advantageously employed as perfuming ingredients, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and at least one perfuming co-ingredient; and
iii) optionally at least one perfumery adjuvant.

By "perfumery carrier" it is meant here a material which is practically neutral from a perfumery point of view, i.e. which does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting examples solvents such as dipropyleneglycol, diethyl phthalate, isopropyl myristate, benzyl benzoate, 2-(2-ethoxyethoxy)-1-ethanol or ethyl citrate, which are the most commonly used. For the compositions which comprise both a perfumery carrier and a perfumery base, other suitable perfumery carriers than those previously specified, can be also water (in which case a solubilizing amount of surfactants may be necessary), ethanol, water/ethanol mixtures, limonene or other terpenes, isoparaffins such as those known under the trademark Isopar (origin: Exxon Chemical) or glycol ethers and glycol ether esters such as those known under the trademark Dowanol® (origin: Dow Chemical Company).

As solid carriers one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloide: Stabilisatoren, Dickungs- and Geliermittel in Lebensmitteln, Band 2 der Schriftenreihe Lebensmittelchemie, Lebensmittelqualität, Behr's Verlag GmbH & Co., Hamburg, 1996. The encapsulation is a well known process to a person skilled in the art, and may be performed, for instance, using techniques such as spray-drying, agglomeration or yet extrusion; or consists of a coating encapsulation, including coacervation and complex coacervation technique.

Said at least one perfuming co-ingredient is not of formula (I). Moreover, by "perfuming co-ingredient" it is meant here a compound, which is used in a perfuming preparation or a composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of his general knowledge and according to the intended use or application and the desired organoleptic effect. In general terms, these perfuming co-ingredients belong to chemical classes as varied as alcohols, lactones, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds, or can be an encapsulated perfume.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfuming co-ingredient, and optionally at least one perfumery adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for his work.

The invention's compound can be advantageously used in many fields of modern perfumery, in particular functional perfumery, to positively impart or modify the odor of a consumer product into which said compound (I) is added. Indeed, for example, the invention's compounds are capable of exploiting the bacteria present in human sweat and to combat related malodor by releasing at the right moment perfuming molecules, levitating problems often encountered with classical perfuming ingredients present as such which in deodorant compositions are already evaporated when their action is actually needed, i.e. when the bacteria is cleaving the malodor precursor.

Consequently, a perfuming consumer product which comprises:
i) as perfuming ingredient, at least one compound of formula (I), as defined above; and
ii) a perfumery consumer base;
is also an object of the present invention.

The invention's compound can be added as such or as part of an invention's perfuming composition.

For the sake of clarity, it has to be mentioned that, by "perfuming consumer product" it is meant a consumer product which is expected to deliver at least a perfuming effect, in other words it is a perfumed consumer product. For the sake of clarity, it has to be mentioned that, by "perfumery consumer base" we mean here the functional formulation, as well as optionally additional benefit agents, corresponding to a consumer product which is compatible with perfuming ingredients and is expected to deliver a pleasant odor to the surface to which it is applied (e.g. skin, textile, or home surface). In other words, a perfuming consumer product according to the invention comprises the functional formulation, as well as optionally additional benefit agents, corresponding to the desired consumer product, e.g. a deodorant or an air freshener, and an olfactive effective amount of at least one invention's compound.

The nature and type of the constituents of the perfumery consumer base do not warrant a more detailed description here, which in any case would not be exhaustive, the skilled person being able to select them on the basis of his general knowledge and according to the nature and the desired effect of said product.

Non-limiting examples of suitable perfumery consumer base can be a fabric care product, such as a liquid or solid detergent, a fabric softener, a fabric refresher, a bleach; a cosmetic preparation such as a deodorant or antiperspirant, or a skin-care product (e.g. a perfumed soap, shower or bath mousse, or a hygiene product); an air care product, such as an air freshener or a "ready to use" powdered air freshener; or a home care product, such a dish detergent or hard-surface detergent.

Preferred perfuming compositions or perfumed articles are deodorants and antiperspirants.

Typical examples of deodorant or antiperspirant compositions into which the compounds of the invention can be incorporated are described e.g. in U.S. Pat. No. 4,822,603, WO2001089464, EP0024175, EP0468564 or EP0384034.

Some of the above-mentioned consumer product bases may represent an aggressive medium for the invention's compound, so that it may be necessary to protect the latter from premature decomposition, for example by encapsulation or by chemically bounding it to another chemical which is suitable to release the invention's ingredient upon a suitable external stimulus, such as an enzyme, light, heat or a change of pH.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 10%, preferably 0.1 to 5% by weight, or even more, of the compounds of the invention based on the weight of the composition into which they are incorporated. Concentrations lower than these can be used when these compounds are incorporated into perfumed articles, percentage being relative to the weight of the article.

A method for liberating a perfuming alcohol from a composition as defined above, comprising the steps of contacting a compound of formula (I) with bacteria having the gene encoding for the β-glucuronidase enzyme (uidA) is another object of the invention. According to a particular embodiment, the bacteria is from human origin and belongs to a family selected from Enterobacteriaceae and the genera *Corynebacterium, Propionibacterium, Streptococcus, Lactobacillus, Bifidobacterium, Clostridium, Bacteroides* and *Corynebacterium*. Preferably the bacteria is identified as one selected from *Propionibacterium acnes, Streptococcus agalactiae, Escherichia coli, Escherichia fergusonii, Staphylococcus warneri, Staphylococcus xylosus, Staphyloccocus haemolyticus, Streptococcus agalactiae, Escherichia coli, Escherichia fergusonii*.

The invention will now be described in further details by way of the following examples, which should not be considered as limiting the invention. In the examples the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacement δ are indicated in ppm with respect to the TMS as standard, the coupling constants J are expressed in Hz.

Example 1

Synthesis of Compounds of Formula (I)

Experimental:
UPLC-MS.
Analyses were performed on a Waters (Baden-Dattwil, Switzerland) Acquity system coupled to a mass spectrometer. The separations were performed on an Acquity BEH-C18 column (2.1 mm i.d.×100 mm, 1.7 μm). The elution solvents were $CH_3CN$ containing 0.1% of formic acid (solvent B) and water containing 0.1% of formic acid (solvent A). The gradient profile started at 10% of B, which was held for 0.5 min, increased to 90% of B in 7.5 min. The flow rate was 0.3 mL/min. The mass spectrometer was a Thermo Finnigan LXQ with an ESI source (HESI-II) operated in negative mode. The spray voltage was 4.0 kV, the vaporizer temperature was 250° C., the capillary temperature was 350° C. The sheath gas was nitrogen at a flow rate of 50 (Finnigan arbitrary units). The auxiliary gas was also nitrogen at a flow rate of 20 (Finnigan arbitrary units). The events were full scan [80-800] which was linked with a data dependent MS/MS of the $1^{st}$ most intense ion from scan event 1, collision energy 35 V. Nuclear Magnetic Resonance (NMR) Spectra. 1H- and 13C-NMR spectra were recorded on a Bruker AV-500 (Zurich, Switzerland) spectrometer at 500.13 and 125.76 MHz or AV-600 spectrometer at 600.34 and 150.96 MHz respectively. The chemical shifts are referenced to TMS as internal standard. The assignments have been confirmed by 2D NMR (HSQC, HMBC and COSY).

(i) Synthesis of 2-phenylethyl β-D-glucopyranosiduronic acid (phenethylol glucuronide)

β-Glucopyranosides were prepared according to standard procedures, starting from commercially available pentaacetylbromo-D-glucose as the glycosyl donor and the free alcohols as the respective glycosyl acceptors.

Phenethylol glucoside (973 mg, 3.42 mmol), PIPO (12 mg), KBr (41 mg, 0.34 mmol) and tetrabutylammonium chloride (57 mg, 0.2 mmol) were mixed in methylene chloride (11 mL) and $NaHCO_3$ sat. (6.6 mL). After cooling at 0° C., a mixture of NaOCl 10% (8.6 mL) and NaCl sat (15 mL) was added dropwise and the reaction was stirred for 1.5 h at room temperature. Methylene chloride was distilled off and the mixture was acidified with concentrated HCl to pH 2-2.5. The product was purified by flash chromatography over RP-18 (water 9:ethanol 1) afforded phenethylol glucuronide (581 mg) in 57% yield. MW: 298.3 ($C_{14}H_{18}O_7$).

UPLC-MS H-ESI$^-$ (r.t. 3.14 min)

MS-MS: M-H=296.9, dependant scan: MS$^n$: 112.6 (100% relative intensity), 156.7 (42), 174.7 (30%), 86.6 (27%), 236.9 (26%), 192.8 (25%).

$^{13}$C NMR (125 MHz, MeOD): δ 37.2 (t), 72.0 (t), 73.7 (d), 74.9 (d), 76.2 (d), 77.8 (d), 104.4 (d), 127.2 (d), 129.4 (d), 130.1 (d), 140.0 (s), 177.4 (s).

(ii) Synthesis of (4-hydroxyphenyl)-2-butanone-β-D-glucopyranosiduronic acid (raspberry ketone glucuronide)

Raspberry ketone glucoside (1000 mg, 3.06 mmol), PIPO (12 mg), KBr (36.5 mg, 0.306 mmol) and tetrabutylammonium chloride (51.1 mg, 0.184 mmol) were mixed in methylene chloride (11 mL) and NaHCO3 sat. (6.6 mL). After cooling at 0° C., a mixture of NaOCl 10% (7.72 mL) and NaCl sat (15 mL) was added dropwise and the reaction was stirred for 2.5 h at R.T. Methylene chloride was distilled off and the mixture was acidified with concentrated HCl to pH 2-2.5. The product was purified by flash chromatography on $SiO_2$ (ethyl acetate 6:methanol 4) afforded raspberry ketone glucuronide 10 (228 mg) in 22% yield.

MW: 340.3 ($C_{16}H_{20}O_8$).

UPLC-MS H-ESI$^-$ (r.t. 2.67 min)

MS-MS: M-H=339, dependant scan: MS$^n$: 112.6 (100% relative intensity), 174.7 (66%), 86.6 (27%), 162.8 (7%).

$^{13}$C NMR (125 MHz, MeOD): δ 30.0 (t), 30.0 (q), 46.0 (t), 73.6 (d), 74.7 (d), 76.4 (d), 77.7 (d), 102.6 (d), 118.1 (d), 130.3 (s), 136.6 (s), 157.6 (s), 177.0 (s), 211.1 (s).

(iii) Synthesis of methyl 2,3,4-tri-O-acetyl-1-O-(2,2,2-trichloroethanimidoyl)-D-glucopyranuronate Methyl 2,3,4-tri-O-acetyl-D-glucopyranuronate (1.5 g, 4.49 mmol) was dissolved in $CH_2Cl_2$ (18 mL) followed by trichloroacetonitrile (4.34 g, 30.1 mmol) and $K_2CO_3$ (4.15 g, 30.1 mmol). The mixture was stirred 15 hours at 21° C. The crude mixture was loaded on a $SiO_2$ column containing (4 cm high, about 6 g $SiO_2$), eluted with $Et_2O$ (100 mL) and concentrated on rotary evaporator to give 1.79 g, 100% α-isomer, yield 83%.

$^{13}$C NMR (125 MHz, $CDCl_3$): δ 20.4 (q), 20.5 (q), 20.7 (q), 53.0 (q), 69.0 (d), 69.1 (d), 69.5 (d), 70.5 (d), 90.5 (s), 92.6 (d), 160.6 (s), 167.2 (s), 169.5 (s), 169.7 (s), 169.8 (s).

(iv) Synthesis of 3,7-dimethyloct-6-en-1-yl β-D-glucopyranosiduronic acid (citronellol glucuronide)

Methyl 2,3,4-tri-O-acetyl-1-O-(2,2,2-trichloroethanimidoyl)-D-glucopyranuronate (190 mg, 0.397 mmol) and citronellol (62 mg, 0.397 mmol) were stirred 1 hour in $CH_2Cl_2$ (7 mL), in presence of molecular sieves 4A. The reaction was cooled down at −15° C., 1 hour. Then $BF_3Et_2O$ (25.4 mg, 0.179 mmol) was added. The reaction was monitored by TLC (thin layer chromatography, $SiO_2$). After 30 min. the whole imidate was consumed. EtOAc was added (30 mL) and the organic phase was washed with $NaHCO_3$ aqueous saturated solution, then with brine. The solvent was removed on rotary evaporator under vacuum. The crude product was purified by flash chromatography on $SiO_2$ (13 g), elution with pentane/$Et_2O$ ⅔ and we obtained 85 mg (yield 45%) of the protected sugar, 100% 13 isomer.

The purified product (74 mg, 0.157 mmol) was diluted in MeOH (2 mL). At 0° C. aqueous NaOH 5 M (0.16 mL) was added. The product was stirred one hour while coming back at room temperature. The MeOH was removed under vacuum, the residue was then loaded in solution in water on a chromatography column (Si=2-RP18, 2.5 g). The column was eluted with a gradient starting at 100% water and the product was in fractions eluted with a mixture of water/EtOH 4/1. We obtained the title compounds as a mixture of two diastereoisomers, pure with a β stereochemistry: 28 mg (yield 54%).

MW: 332.4 ($C_{16}H_{28}O_7$)

UPLC-MS H-ESI$^-$ (r.t. 4.93 min)

MS-MS: M-H=331.2 dependant scan: MS$^n$: 112.6 (100% relative intensity), 156.7 (58%), 128.7 (39%), 271.0 (36%).

$^{13}$C NMR (151 MHz, MeOD) (* stereoisomer): 17.6 (q); 20.0 (q); 25.9 (q); 26.5 (t); 30.7 (t); 30.7 (t); 73.6 (d); 69.3, 69.4* (t); 73.7, 75.0* (d); 75.0, 76.1* (d); 77.9 (d); 104.3, 104.4* (d); 125.9, 126.0 (s); 177.0 (s).

(v) Synthesis of 2,6-dimethyloct-7-en-2-yl β-D-glucopyranosiduronic acid (dihydromyrcenol glucuronide)

Methyl 2,3,4-tri-O-acetyl-1-O-(2,2,2-trichloroethanimidoyl)-D-glucopyranuronate (190 mg, 0.397 mmol) and dihydromyrcenol (62 mg, 0.397 mmol) were stirred 1 hour in presence of molecular sieves 4A. The reaction was cooled down at −15° C. (1 hour). Then $BF_3Et_2O$ (25.4 mg, 0.179 mmol) was added. The reaction was monitored by TLC (thin layer chromatography, $SiO_2$). After 30 min. the whole imidate was consumed. EtOAc was added (30 mL) and the organic phase was washed with $NaHCO_3$ aqueous saturated solution, then with brine. The solvent was removed on rotary evaporator under vacuum. The crude product was purified by flash chromatography on $SiO_2$ (13 g), elution with pentane/$Et_2O$ ⅔ and we obtained 73 mg (yield 39%) of the protected sugar, 100% 13 isomer.

The purified product (60 mg, 0.127 mmol) was diluted in MeOH (2 mL). At 0° C. aqueous NaOH 5 M (0.13 mL) was added. The product was stirred one hour while coming back at room temperature. The MeOH was removed under vacuum, the residue was then loaded in solution in water on a chromatography column (Si=2-RP18, 2.5 g). The column was eluted with a gradient starting at 100% water and the product was in fractions eluted with a mixture of water/EtOH 4/1. We obtained the title compounds as a mixture of two diastereoisomers, pure with a 13 stereochemistry: 21 mg (yield 50%).

MW: 332.4 ($C_{16}H_{28}O_7$).

UPLC-MS H-ESI⁻ (r.t. 4.64 min)

MS-MS: M-H=331.2 dependant scan: MS″: 112.6 (100% relative intensity), 156.7 (47%), 128.7 (29%), 174.8 (7%).

$^{13}C$ NMR (151 MHz, MeOD) (* stereoisomer): 20.1 (q); 23.0 (t); 26.8 (q), 38.5 (t); 39.1 (d); 48.6, 48.7* (t); 73.8 (t); 75.0 (d); 76.5 (t); 78.1 (d); 79.2 (s); 98.5 (d); 112.9 (t); 146.1 (d); 177.0 (s).

Example 2

Performance of Compounds of Formula (I) as "Pro-Perfume"

The liberation of perfuming alcohols from the present invention's compounds of formula (I) was tested in vitro during incubation with defined skin bacteria strains.

Incubations

1. Preparation of Bacterial Solution a) Media: Trypticase Soja Agar (TSA) solid medium was purchased from Beckton Dickinson, Pont de Claix, France. Schaedler agar containing 5% sheep blood (SCH) solid medium was purchased from Biomerieux, Lyon, France.

b) Reagent: sterile Sodium Chloride solution at 0.9% (NaCl 0.9%) was prepared in the laboratory. Sodium Chloride powder was purchased from Carlo Erba, Val de Reuil, France.

c) Bacterial solutions: Two underarm bacterial isolates, *Propionibacterium acnes* ATCC 6919 and *Staphylococcus warneri* DSM 20316 (identified by 16S rDNA sequencing by Deutsche Sammlung von Mikroorganismen and ZellKulturen DSMZ, Germany), were cultivated on SCH agar at 37° C. during 72 h in anaerobic conditions and on TSA at 37° C. during 24 h, respectively.

One isolated colony of *P. acnes* from the pure primary culture on SCH agar was inoculated on a new SCH agar and incubated at 37° C., 72 h in anaerobic conditions. After incubation, the whole culture was dissociated by shaking in 20 ml of NaCl 0.9% then centrifuged 10 min at 5000 rpm at room temperature. The pellet was washed in NaCl 0.9% and concentrated two times in NaCl 0.9%.

Similarly, one colony of *S. warneri* from the pure primary culture on TSA was inoculated on a new TSA and incubated for 24 h at 37° C. After incubation, the whole culture was dissociated by shaking in 20 ml of NaCl 0.9% then centrifuged 15 min at 5000 rpm, 4° C. The pellet was washed in NaCl 0.9% and concentrated two times in NaCl 0.9%.

2. General Method for Incubation

A pro-perfume glucuronides mixture containing menthol glucuronide (6 mg/kg), phenethylol β-glucuronide (10.75 mg/kg) and raspberry ketone β-glucuronide (13 mg/kg) in water was incubated with either:

500 μL of the previously described bacterial solution
  10 μL of commercial enzymes β-glucuronidase/arylsulfatase from *Helix pomatia* (RocheDiagnostic, Indianapolis, USA) and 490 μL of NaCl 0.9% as a positive control
  500 μl of NaCl 0.9% as a negative control for the incubation with bacteria.

Each solution was prepared in duplicate (in glass vials).

The vials were placed in a heating block at 37° C. under gentle stirring from 1 to 7 days depending on the bacteria solutions. At the end of the incubation time, vials were cooled down to room temperature, 150 μL was mixed with 50 μL of LC-MS solvent B, filtered through acrodisc and 1 μL was injected on LC-MS (peak areas considered were measured in SIM mode according to their respective molecular weights). Comparisons were made between glucuronides (HESI−) or glucosides (HESI+) areas in incubated solutions and glucuronides (HESI−) or glucosides (HESI+) areas in the blanks (fixed as 100%).

3. Analysis of the Volatiles after Incubation

General Method

In a 2 mL glass vial, a solution of Internal Standard (IS) (Eicosane) in $CH_2Cl_2$ (200 μL, 0.2 μg) and 200 μL of $CH_2Cl_2$ were added to the solution of incubation, well mixed then centrifuged at 3260 g for 3 min. The lower layer was removed with a pipette, dried on $Na_2SO_4$ filtered on cotton and concentrated under on argon flow to about 20 μL. 1 μL was injected onto the GC-MS. The concentration was determined from the GC-MS peak areas of a-androstenol (m/z 274) compare to the a-androstanol (m/z 276) and corrected by the response factor value (0.3845±0.03).

TABLE 1

Glucuronide-conjugates remaining after incubation with *Propionibacterium acnes* (in percentage)

| | Released corresponding alcohol | | |
|---|---|---|---|
| | raspberry ketone | 2-phenylethanol | p-menthan-3-ol |
| After 1 day | No transformation | | |
| After 5 days | | | |
| incubation 1 | 61 | 94 | 5 |
| incubation 2 | 58 | 85 | 9 |
| incubation 3 | 57 | 84 | 7 |
| Average | 58 | 88 | 7 |

TABLE 2

Glucuronide-conjugates remaining after incubation with *S. warneri* (in percentage).

| | Released corresponding alcohol | | |
|---|---|---|---|
| | raspberry ketone | 2-phenylethanol | p-menthan-3-ol |
| After 1 day | | | |
| incubation 1 | 0 | 0 | 1 |
| incubation 2 | 0 | 0 | 0 |
| Average | 0 | 0 | 0 |

The data show that in presence of *Propionibacterium acnes*, while no transformation is observed after 1 day, alcohols are released after 5 days incubation. Turning to *Staphylococcus warneri*, there is a complete transformation and no remaining starting material after only 1 day, which demonstrates a quicker release of the corresponding alcohols.

TABLE 3

Glucuronide-conjugates remaining after incubation with *S. warneri* (in percentage).

| | Released corresponding alcohol | | |
|---|---|---|---|
| | vanilline | eugenol | menthol |
| After 1 day | | | |
| incubation 1 | 84 | 130 | 72 |
| incubation 2 | 96 | 120 | 77 |
| Average | 100 | 100 | 74 |
| After 5 day | | | |
| incubation 1 | 0 | 0 | 36 |
| incubation 2 | 0 | 0 | 31 |
| Average | 0 | 0 | 34 |

The results show an efficient release of alcohols from glucoside conjugates after 5 day-incubation with *S. warneri*.

What is claimed is:

1. A method to confer, enhance, improve or modify the odor properties of a perfuming composition comprising at least one perfumery carrier and at least a perfuming co-ingredient or of a perfumed article, which method comprises adding to said composition or article a perfuming ingredient of a compound of formula (I):

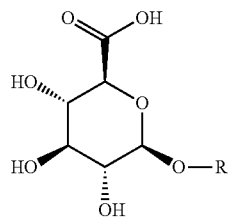

wherein:

R represents an perfuming alcohol selected from the group consisting of 4-allyl-2-methoxyphenol, 3-benzyl-3-pentanol, 4-cyclohexyl-2-methylbutan-2-ol, 2-cyclohexylpropanol, decanol, 9-decenol, (2,4-dimethylcyclohex-3-enyl)methanol, (2,4-dimethylcyclohexyl)methanol, 2-(1,1-dimethylethyl)-4-methylcyclohexanol, 2,6-dimethylheptan-2-ol, 3,7-dimethyl-7-hydroxyoctanal, 2,5-dimethyl-2-indanmethanol, 3,7-dimethyl-1,6-nonadien-3-ol, 6,8-dimethylnonan-2-ol, 4,8-dimethyl-7-nonen-2-ol, (E)-3,7-dimethyl-2,6-octadienol, (Z)-3,7-dimethyl-2,6-octadienol, 3,7-dimethyl-3,6-octadienol, 3,7-dimethyl-1,6-octadien-3-ol, 3,7-dimethyloctane-1,7-diol, 3,7-dimethyloctanol, 2,6-dimethyloctan-2-ol, 3,7-dimethyloctan-3-ol, 3,7-dimethylocten-3-ol, 3,7-dimethyloct-6-enol, 3,7-dimethyloct-7-enol, 2,6-dimethyloct-7-en-2-ol, (E)-3,3-dimethyl-5-(2,2,3-trimethyl-3-cyclopenten-1-yl)-4-penten-2-ol, dodecanol, 1,8-epoxy-p-menthane, 2-ethoxy-5-(1-propenyl)phenol, 2-ethyl-1-hexanol, ethyl 3-hydroxy hexanoate, 4-ethyl-2-methoxyphenol, 6-ethyl-3-methyl-5-octenol, 5-ethylnonan-2-ol, 2-ethyl-4-(2,2,3-trimethylcyclopent-3-enyl)but-2-enol, 1-heptanol, hexanol, hexan-2-ol, 3-hexenol, 4-hexenol, 3-hydroxybutan-2-one, 4-hydroxy-3-ethoxybenzaldehyde, 4-hydroxy-3-methoxybenzaldehyde, 4-(4-hydroxy-3-methoxyphenyl)butan-2-one, 2-(hydroxymethyl)nonan-2-one, 4-(4-hydroxy-1-phenyl)butan-2-one, 1-(N-indolyl)-3,7-dimethyloctane-1,7-diol, 4-isopropyl-1-benzenemethanol, 4-isopropylcyclohexanol, 1-(4-isopropyl-1-cyclohexyl)ethanol, (4-isopropyl-1-cyclohexyl)methanol, 2-isopropyl-5-methylphenol, 5-isopropyl-2-methylphenol, (4-isopropylphenyl)methanol, 7-p-menthanol, p-menthan-3-ol, p-menthan-8-ol, p-menthen-4-ol, p-menthen-8-ol, p-menth-8-enol, p-menth-8-en-2-ol, p-menth-8-en-3-ol, 4-methoxy-1-benzenmethanol, 7-methoxy-3,7-dimethyloctan-2-ol, 2-methoxy-4-methylphenol, 2-methoxyphenol, 2-methoxy-2-phenylethanol, (4-methoxyphenyl)methanol, 2-methoxy-4-(1-propenyl)phenol, 2-methoxy-4-propyl-1-cyclohexanol, 2-methoxy-4-propylphenol, 2-methoxy-4-vinylphenol, 3-(4-methylcyclohex-3-enyl)butanol, 4-methyl-3-decenol, 4-methyl-3-decen-5-ol, 4-(1-methylethyl)cyclohexylmethanol, 4-methylphenol, 2-methyl-4-phenylbutan-2-ol, 3-methyl-4-phenylbutan-2-ol, 1-(4-methylphenyl)ethanol, 2-(2-methylphenyl)ethanol, 2-methyl-4-phenylpentanol, 2-methyl-5-phenylpentanol, 3-methyl-5-phenylpentanol, 4-methyl-1-phenylpentan-2-ol, 2-methyl-1-phenylpropan-2-ol, 2-(4-methylphenyl)propan-2-ol, 3-methyl-5-(2,2,3-trimethyl-3-cyclopenten-1-yl)-4-penten-2-ol, 2-(2-methylpropyl)-4-hydroxy-4-methyl-tetrahydropyrane, 2-methyl-4-(2,3,3-trimethyl-2-cyclopenten-1-yl)-2-butenol, 3-methyl-5-(2,2,3-trimethyl-3-cyclopenten-1-yl)pentan-2-ol, 2-methyl-4-(2,2,3-trimethyl-3-cyclopenten-1-yl)pent-4-enol, 3-methyl-5-(2,2,3-trimethylcyclopentyl-3-enyl)pent-4-en-2-ol, 2,6-nonadienol, 1-nonanol, 6-nonenol, 1,2,3,4,4a,5,8,8a-octahydro-2,2,6,8-tetramethyl-1-naphthalenol, octahydro-2,5,5-trimethyl-2-naphthalenol, octanol, octan-2-ol, octan-3-ol, 1-octen-3-ol, 3,4,5,6,6-pentamethylheptan-2-ol, 2-pentyl-1-cyclopentanol, perhydro-4,8a-dimethyl-4a-naphthalenol, 2-phenoxyethanol, 4-phenylbutan-2-ol, 4-phenyl-3-buten-2-ol, 1-phenylethanol, 2-phenylethanol, 1-phenylhexan-2-ol, phenylmethanol, 1-phenylpentan-2-ol, 2-phenylpropanol, 2-phenylpropanol, 3-phenylpropanol, 1-phenylpropan-2-ol, 3-phenyl-2-propenol, 2-tert-butylcyclohexanol, 4-tert-butylcyclohexanol, 1-(2-tert-butyl-cyclohexyloxy)butan-2-ol, 2-tert-butyl-4-methyl-1-cyclohexanol, tetrahydro-2-isobutyl-4-methyl(2H)pyran-4-ol, 2-(tetrahydro-5-methyl-5-vinyl-2-furyl)propan-2-ol, 1-(2,2,3,6-tetramethylcyclohex-1-yl)hexan-3-ol, 2,4,6,8-tetramethylnonan-1-ol, 3,6,7-tetramethylnonan-1-ol, 2,6,10,10-tetramethyl-1-oxaspiro[4.5]decan-6-ol, 2,6,6,8-tetramethyltricyclo[5.3.1.0(1,5)]undecan-8-ol, (+)-(1R,2R)-1,3,3-trimethylbicyclo[2.2.1]heptan-2endo-ol, (+)-(1R,2S)-1,7,7-trimethylbicyclo[2.2.1]heptan-2-ol, 2,6,6-trimethylbicyclo[3.1.1]heptan-3-ol, 3-(5,5,6-trimethylbicyclo[2.2.1]hept-2-yl)cyclohexanol, 4-(5,5,6-trimethylbicyclo[2.2.1]hept-2-yl)cyclohexanol, 3,3,5-trimethylcyclohexanol, 4-(2,6,6-trimethyl-2-cyclohexen-1-yl)butan-2-ol, 4-(2,6,6-trimethyl-1-cyclohexen-1-yl)-3-buten-2-ol, (E)-4-(2,6,6-trimethyl-2-cyclohexen-1-yl)-3-buten-2-ol, (2,4,6-trimethylcyclohex-3-enyl)methanol, 1-(2,2,6-trimethyl-1-cyclohexyl)hexan-3-ol, 5-(2,2,3-trimethyl-3-cyclopentenyl)-3-methylpentan-2-ol, 4,7,9-trimethyldecan-2-ol, 4,6,8-trimethyldecan-2-ol, 3,8,9-trimethyldecan-2-ol, 3,7,11-trimethyl-1,6,10-dodecatrien-3-ol, 3,3,5-trimethylhexanol, undecanol, undecan-2-ol and 10-undecenol so that the perfuming alcohol is released through contact of the perfuming ingredient with skin microflora, human sweat, or a bacterium from the surrounding environment.

2. A method to confer, enhance, improve or modify the odor properties of a perfuming composition comprising at least one perfumery carrier and at least a perfuming co-ingredient or of a perfumed article, which method comprises adding to said composition or article a perfuming ingredient of a compound of formula (I):

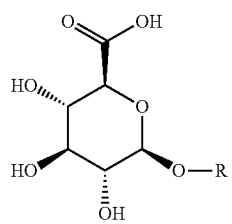

wherein R is selected from the group consisting of (E)-3,7-dimethyl-2,6-octadienol, 3,7-dimethyl-1,6-octadien-3-ol, 3,7-dimethyloct-6-enol, 2,6-dimethyloct-7-en-2-ol, 3-hexenol, 2-phenylethanol, (E)-3,3-dimethyl-5-(2,2,3-trimethyl-3-cyclopenten-1-yl)-4-penten-2-ol, 7-p-menthanol, 3-methyl-5-phenylpentanol, 2,6-nonadienol, 1-phenylhexan-2-ol, tetrahydro-2-isobutyl-4-methyl(2H)pyran-4-ol, 3-(5,5,6-trimethylbicyclo[2.2.1]hept-2-yl)cyclohexanol,3-(4-methylcyclohex-3-enyl)butanol, 4-cyclohexyl-2-methylbutan-2-ol, 4-methyl-3-decen-5-ol, 4-allyl-2-methoxyphenol, 4-(4-hydroxy-1-phenyl)butan-2-one, p-menthan-3-ol, 4-hydroxy-3-methoxybenzaldehyde, 3,7-dimethyl-1,6-nonadien-3-ol, 3,7-dimethyloctanol, 1-(2,2,6-trimethyl-1-cyclohexyl)hexan-3-ol, 2-ethyl-4-[2,2,3-trimethylcyclopent-3-enyl)but-2-enol, (E)-3,3-dimethyl-5-(2,2,3-trimethyl-3-cyclopenten-1-yl)-4-penten-2-ol and 2-(1,1-dimethylethyl)-4-methylcyclohexanol so that the perfuming alcohol is released through contact of the perfuming ingredient with skin microflora, human sweat, or a bacterium from the surrounding environment.

3. The method of claim 2, characterized in the R is selected from the group consisting of 4-allyl-2-methoxyphenol, 4-(4-hydroxy-1-phenyl)butan-2-one, p-menthan-3-ol, 4-hydroxy-3-methoxybenzaldehyde, 2-phenyl ethanol, 3,7-dimethyloct-6-enol and 2,6-dimethyloct-7-en-2-ol.

4. A method according to claim 1 wherein the perfuming alcohol is liberated into the perfuming composition or perfumed article by contacting the compound of formula (I) with bacteria having the gene encoding the β-glucuronidase enzyme (uidA).

5. A method according to claim 4, characterized in that the bacteria is from human origin and belongs to a family selected from Enterobacteriaceae and the genera *Corynebacterium*, *Propionibacterium*, *Streptococcus*, *Lactobacillus*, *Bifidobacterium*, *Clostridium*, *Bacteroides* and *Corynebacterium*.

6. A method according to claim 5, wherein the bacteria is identified as one selected from *Propionibacterium acnes*, *Streptococcus agalactiae*, *Escherichia coli*, *Escherichia fergusonii*, *Staphylococcus warneri*, *Staphylococcus xylosus*, *Staphyloccocus haemolyticus*, *Streptococcus agalactiae*, *Escherichia coli* and *Escherichia fergusonii*.

7. A method according to claim 1, wherein the perfuming alcohol p-menthan-3-ol is liberated into the perfuming composition or perfumed article by contacting the compound of formula (I) wherein R is p-menthan-3-ol with *Staphylococcus warneri*.

8. A method according to claim 7, wherein the compound is added to a perfuming composition comprising at least one ingredient selected from the group consisting of a perfumery carrier and at least a perfuming co-ingredient; and optionally at least one perfumery adjuvant.

9. A method according to claim 7, wherein the compound is added to a perfuming consumer product which comprises a perfumery consumer base.

10. A method according to claim 9, wherein the perfumery consumer base is a liquid or solid detergent, a fabric softener, a fabric refresher, a bleach, a deodorant or antiperspirant, a perfumed soap, shower or bath mousse, a hygiene product, an air freshener, a "ready to use" powdered air freshener, a dish detergent or hard-surface detergent.

11. A method according to claim 9, wherein the perfumery consumer base is a deodorant or antiperspirant.

12. A method according to claim 1, wherein the compound is added to a perfuming composition comprising at least one ingredient selected from the group consisting of a perfumery carrier and at least a perfuming co-ingredient; and optionally at least one perfumery adjuvant.

13. A method according to claim 1, wherein the compound is added to a perfuming consumer product which comprises a perfumery consumer base.

14. A method according to claim 13, wherein the perfumery consumer base is a liquid or solid detergent, a fabric softener, a fabric refresher, a bleach, a deodorant or antiperspirant, a perfumed soap, shower or bath mousse, a hygiene product, an air freshener, a "ready to use" powdered air freshener, a dish detergent or hard-surface detergent.

15. A method according to claim 13, wherein the perfumery consumer base is a deodorant or antiperspirant.

16. A method according to claim 1 wherein the perfuming composition also includes at least one perfumery adjuvant.

17. A method according to claim 2 wherein the perfuming composition also includes at least one perfumery adjuvant.

* * * * *

UNITED STATES PATENT AND TRADEMARK OFFICE
CERTIFICATE OF CORRECTION

| | | |
|---|---|---|
| PATENT NO. | : 9,550,960 B2 | Page 1 of 1 |
| APPLICATION NO. | : 14/899556 | |
| DATED | : January 24, 2017 | |
| INVENTOR(S) | : Starkenmann et al. | |

It is certified that error appears in the above-identified patent and that said Letters Patent is hereby corrected as shown below:

In the Claims

Column 14:
Lines 41-42, delete "1-(2-tert-butyl-cyclohexyl oxy butan-2-ol," and insert
-- 1-(2-tert-butyl-cyclohexyloxy butan-2-ol, --.

Column 15:
Line 44, delete "2-phenyl ethanol," and insert -- 2-phenylethanol, --.

Signed and Sealed this
Seventh Day of March, 2017

Michelle K. Lee
*Director of the United States Patent and Trademark Office*